United States Patent [19]

Schelbeck

[11] Patent Number: Plant 5,887

[45] Date of Patent: Feb. 24, 1987

[54] BEGONIA PLANT

[75] Inventor: Erland V. Schelbeck, Odense, Denmark

[73] Assignee: L. Daehnfeldt A/S, Odense, Denmark

[21] Appl. No.: 690,287

[22] Filed: Jan. 10, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Olson and Olson

[57] ABSTRACT

A new and distinctive cultivar of Begonia plant bearing medium sized, heavily filled flowers of rose color and small, medium green, tapered leaves. The plant is characterized by rapid propagation and vigorous growth, producing flowers and leaves of long persistance and excellent display.

1 Drawing Figure

BACKGROUND OF THE INVENTION

This invention relates to a new and distinctive cultivar of Begonia plant known botanically as *Begonia hiemalis* Begonia (Fotch) and known by the cultivar name Grete.

This new cultivar was discovered by me as a seedling from a controlled crossing of tuberous seedling P 518 as the seed parent with Begonia socotrana as the pollen parent.

Asexual reproduction by stem and/or leaf cuttings has reproduced the unique features of the new cultivar through successive propagations.

The following characteristics distinguish the new begonia from both its parents and other begonias commercially known and used in the floriculture industry:

(1) The new cultivar is very compact and has small medium green tapered leaves.

(2) The flowers are medium-sized and heavily filled of a nice attractive rose colour.

(3) The cultivar propagates rapidly and uniformly by leaf cuttings.

(4) Foliage and flowers are in good proportion, presenting excellent display.

(5) The keeping quality of the flowers and the foliage in all seasons allows production and sales efficiencies to be maximized.

(6) The new cultivar tends to be very vigorous so that 10 cm (4 inches) pot production is best done with shoot cuttings and tip pinching.

(7) Propagation by leaf cuttings is difficult under light and high temperatures in summer months. Stem cuttings can easily be produced in this season.

(8) The flower colour of Grete undergoes no or very little fading.

(9) The cultivar is compact and can be grown without growth regulators Cycocel and A-rest, but it responds well to these regulators.

THE DRAWING

The accompanying color photograph illustrates the overall appearance of this cultivar taken as a face view of the plant and showing the colors as true as it is reasonably possible to obtain in a colored reproduction of this type.

DESCRIPTION OF THE NEW VARIETY

The following is a detailed description of my new begonia cultivar based on plants produced under commercial practices in glasshouses in various places in Denmark. Color references are made to The Royal Horticultural Society Colour Chart, except where general color terms of ordinary dictionary significance are used.

Parentage: Seed parent tuberous multiflora maxima crossed with species socotrana.

Propagation:

*Type cutting.*—Tip or shoot cuttings 2–3 cm (0.75–1.25 inches) long.

*Time to root.*—27–30 days at 21° C. in summer; 30–35 days at 21° C. in winter.

*Tooting habit.*—Abundant, fibrous.

THE PLANT

Form: Low, compact, self-branching, herbaceous.

Habit of growth: Rapid; upright, strong, short stems.

Foliage: Leaves simple, alternate, borne on vigorous petioles.

(1) *Size.*—8–10 cm (3–4 inches) long and 6–8 cm (2.4–3 inches) wide.

(2) *Shape.*—Entire, broad.

(3) *Texture.*—Firm.

(4) *Margin.*—Serrated.

(5) *Color.*—Young foliage top side; medium green; under side; light green; slightly reddening. Mature foliage top side; dark green; under side; light green, slightly reddening.

(6) *Veination.*—Palmate.

THE FLOWER

Flowering habits: Flowering in racemes with several clusters arising from the stem nodes at the same time giving a highly floriferous appearance. Flowering is continuous for long periods.

Natural flowering season: All seasons.

Flower bud: Flat, oval, light rose color.

Flowers borne: On sturdy pedicels within the form of the raceme.

Quantity: Very floriferous.

Tepals:

(1) *Shape.*—Round.

(2) *Color.*—With regard to the outermost tepal, the edge of the upperside is orange rose (Horticulture Color Chart HCC 620-620/1); the middle of the upperside is orange rose (HCC 620); and the middle of the upperside is red (HCC 19/2). With regard to the innermost, tepal, the edge of the upperside and the middle of the upperside are orange rose (HCC 620) and the middle of the underside is light carmine rose (HCC 621/1).

(3) *Number.*—24–30.

(4) *Size.*—Basal from 35 mm (1.4 inches), interior tepals 15 mm (0.6 inches).

(5) *Flower size.*—4–6 cm (1.5–2.4 inches).

Reproductive organs:

*Stamens.—None.*

Cultivar.—is sterile.

Disease resistance: Appears to have above average resistance to powdery mildew.

I claim:

1. A new and distinct cultivar of *Begonia hiemalis* plant named Grete, as shown and described, and particularly characterized by its medium-sized, heavily filled rose flowers, fast propagation, rapid flowering and its resistance to powdery mildew.

* * * * *

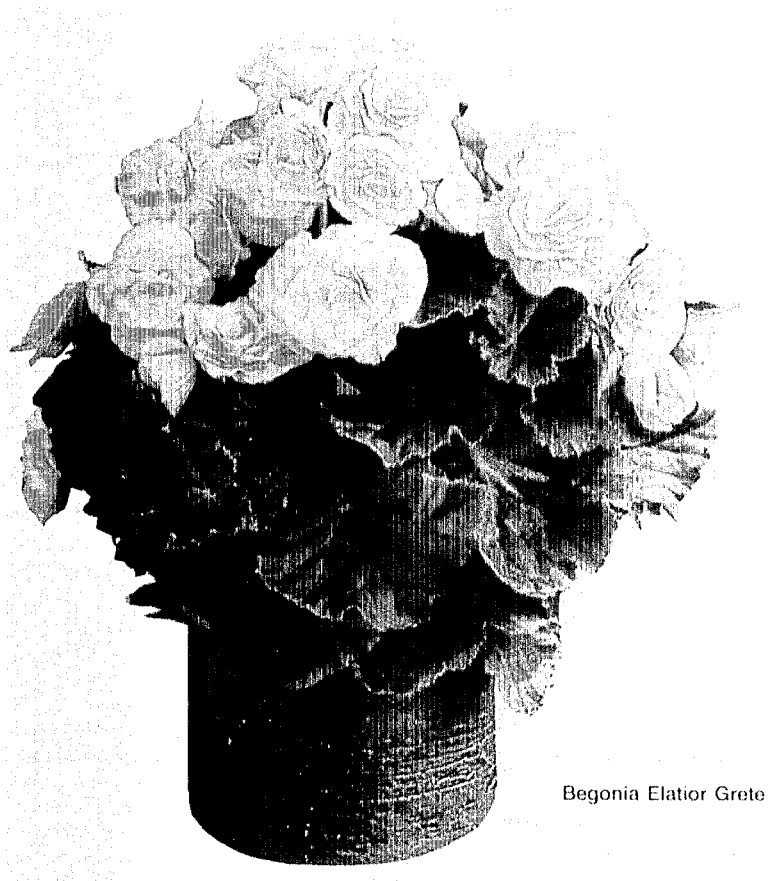
Begonia Elatior Grete

UNITED STATES PATENT AND TRADEMARK OFFICE

CERTIFICATE OF CORRECTION

PATENT NO. : PP 5,887

DATED : February 24, 1987

INVENTOR(S) : Erland V. Schelbeck

It is certified that error appears in the above-identified patent and that said Letters Patent is hereby corrected as shown below:

Column 2, line 14, " Tooting" should read -- Rooting --.

Signed and Sealed this

Ninth Day of June, 1987

*Attest:*

DONALD J. QUIGG

*Attesting Officer*

*Commissioner of Patents and Trademarks*

UNITED STATES PATENT AND TRADEMARK OFFICE

CERTIFICATE OF CORRECTION

PATENT NO. : PP 5,887

DATED : 24 February 1987

INVENTOR(S) : Erland V. Schelbeck

It is certified that error appears in the above-identified patent and that said Letters Patent are hereby corrected as shown below:

Column 2, line 14, "Tooting" should read -- Rooting --.

Column 3, line 1, "upperside" should read -- underside --.

This Certificate supersedes Certificate of Correction issued June 9, 1987.

Signed and Sealed this

Twenty-fifth Day of August, 1987

*Attest:*

DONALD J. QUIGG

*Attesting Officer*

*Commissioner of Patents and Trademarks*